US00PP37755P2

(12) United States Plant Patent
Nelson et al.

(10) Patent No.: US PP37,755 P2
(45) Date of Patent: Oct. 13, 2026

(54) STRAWBERRY PLANT NAMED 'S4A-334'

(50) Latin Name: *Fragaria ananassa*
Varietal Denomination: S4A-334

(71) Applicant: PLANT SCIENCES GENETICS, INC., Watsonville, CA (US)

(72) Inventors: Michael D. Nelson, Watsonville, CA (US); Samuel Estrada Trujillo, Watsonville, CA (US); Craig Mitchell Richael, Meridian, ID (US); Michele Lorraine Krucker, Boise, ID (US); Vanessa Nichole Roullier, Kuna, ID (US)

(73) Assignee: Plant Sciences Genetics, Inc., Watsonville, CA (US)

( * ) Notice: Subject to any disclaimer, the term of this patent is extended or adjusted under 35 U.S.C. 154(b) by 0 days.

(21) Appl. No.: 19/333,301

(22) Filed: Sep. 18, 2025

(51) Int. Cl.
*A01H 5/02* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./209, 208
CPC ..... A01H 5/0893
See application file for complete search history.

(56) References Cited

U.S. PATENT DOCUMENTS

PP29,794 P2 11/2018 Nelson et al.

OTHER PUBLICATIONS

U.S. Appl. No. 19/249,955, filed Jun. 25, 2025, Plant Sciences Genetics, Inc.

*Primary Examiner* — Kent L Bell
(74) *Attorney, Agent, or Firm* — Foley & Lardner LLP

(57) ABSTRACT

This invention relates to a new and distinct variety of strawberry plant named 'S4A-334'. This new strawberry plant named 'S4A-334' is primarily adapted to the growing conditions of the central coast of California, and is primarily characterized by its orange red fruit, very firm flesh, very good flavor, with conical fruit with none or very slight differences in shape between primary and secondary fruit; and fruiting trusses that are typically above foliage with little to no anthocyanin.

7 Drawing Sheets

Latin name of the genus and species of the plant claimed: *Fragaria ananassa.*

Variety denomination: 'S4A-334'.

BACKGROUND OF THE INVENTION

The present invention relates to a new and distinct strawberry plant variety named 'S4A-334'. This new variety is a result of using CRISPR-Cas9 to target a gene which controls flowering habit in the 'Inspire' variety (U.S. Plant Pat. No. 29,794), to suppress its function and alter the plant phenotype, resulting in increased flowering and fruit yield. The target gene is a floral repressor, and its expression is altered by photoperiod and temperature. As temperature and day-length increases, expression of the gene also increases, and flower production is reduced. The knockout of 3 or more alleles of the target gene in short-day strawberry varieties can result in a spectrum of flowering changes, including earlier flowering, increased flowering, insensitivity to day-length in flowering response (day-neutrality), and/or increased fruit yield. In the case of the genetically edited strawberry variety 'S4A-334,' the knockout of alleles in the gene resulted in partial day-neutrality flowering, earlier flowering, and increased flowering and fruiting across the entire fruit harvest season, compared to the non-edited original variety 'Inspire' (U.S. Plant Pat. No. 29,794).

The variety is botanically known as *Fragaria ananassa.*

The genetic edit was made in in Boise, Idaho in 2020 and was selected from a control trial plot in Ventura County, California. After its selection, the new variety was asexually propagated by stolons in both Siskiyou County, California and San Joaquin County, California. The new variety was extensively tested over the next several years in fruit production fields in Ventura County, California. This propagation has demonstrated that the combination of some phenotypic traits along with genotypic data (as disclosed herein) as characterizing the novel variety are fixed and remain true-to-type through successive generations of asexual reproduction.

BRIEF SUMMARY OF THE INVENTION

'S4A-334' is primarily adapted to the climate and growing conditions of the central coast of California. The nearby Pacific Ocean provides the humidity and moderate temperatures needed to produce a strong, vigorous plant and maintain fruit quality during the winter and spring production months.

The following traits have been repeatedly observed and are determined to be unique characteristics of 'S4A-334', which in combination distinguish this strawberry plant as a new and distinct variety:

1. Orange red fruit color;
2. Very firm fruit flesh;

3. Very good flavor;
4. Early flowering; and
5. Fruiting trusses are typically above foliage with little to no anthocyanin.

The closest comparison variety is 'S4A-293' (co-pending U.S. Plant patent application Ser. No. 19/249,955). In side-by-side comparison 'S4A-334' and 'S4A-293' (U.S. Ser. No. 19/249,955) differ by the following combination of characteristics as described in Table 1.

TABLE 1

| Characteristic | 'S4A-334' | 'S4A-293' (U.S. Ser. No. 19/249,955) |
|---|---|---|
| Fruit: Yield | Lower yielding | Higher yielding |
| Type of bearing | Partially remontant | Not remontant |
| Time of flowering | November | December |
| Plant: vigor | Medium | Ranges from medium to strong |

'S4A-334' differs from its antecedent 'Inspire' (U.S. Plant Pat. No. 29,794) by the following combination of characteristics as described in Table 2.

TABLE 2

| Characteristic | 'S4A-334' | 'Inspire' (U.S. Plant Pat. No. 29,794) |
|---|---|---|
| Plant: vigor: | Ranges from medium to strong | Medium |
| Fruit: Yield | Higher yielding | Lower yielding |
| Flowering quantity (season avg) | Ranges from medium to many | Medium |
| Time of flowering | November | December |

BRIEF DESCRIPTIONS OF THE PHOTOGRAPHS

The accompanying color photographs illustrate the overall appearance of typical specimens of the new strawberry variety 'S4A-334' at various stages of development, as true as it is reasonably possible with color reproductions of this type.

Color in the photographs may differ slightly from the color value cited in the botanical descriptions which accurately describe the color of 'S4A-334'.

The depicted plant and plant parts of the new strawberry variety 'S4A-334' are approximately five to seven months old.

The photographs were taken in Ventura County, California.

Figure 1:
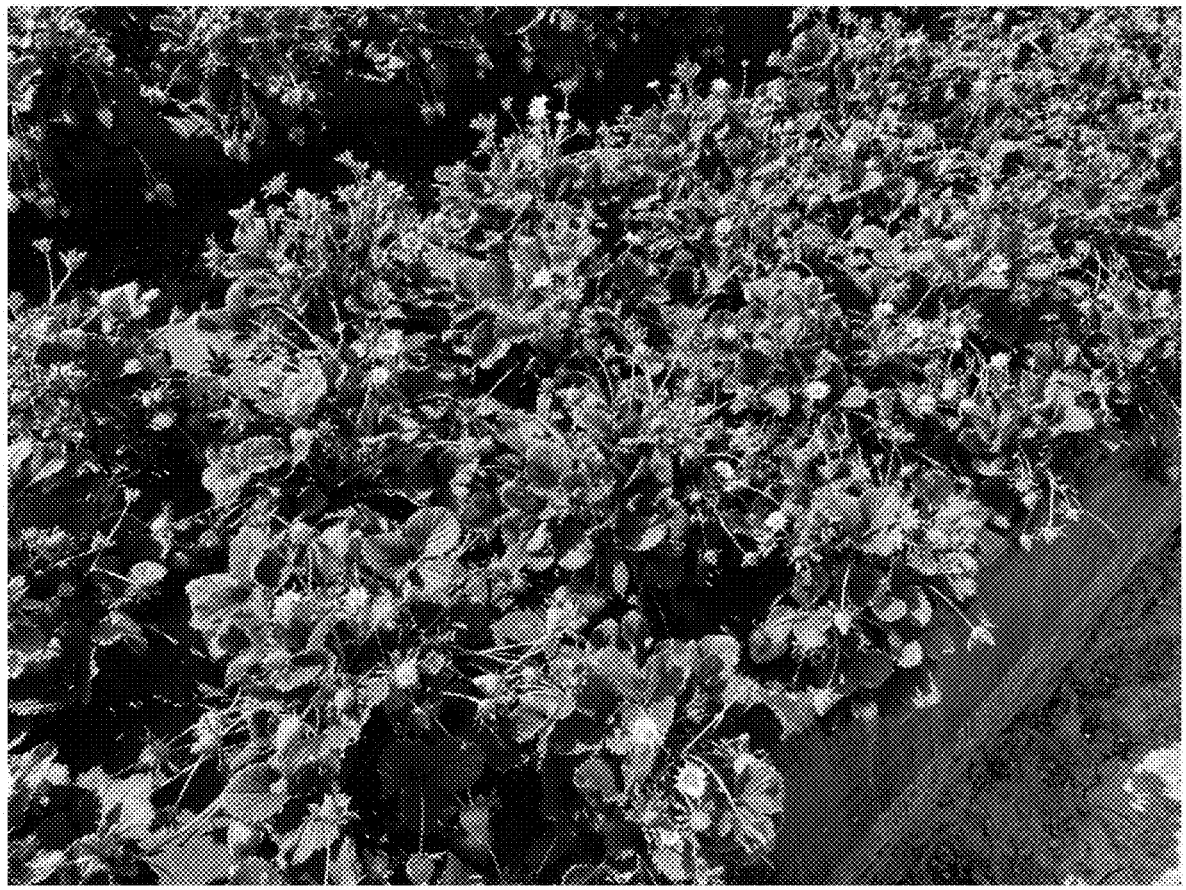
FIG. 1 shows fruiting field characteristics of 'S4A-334', taken in the month of March 2024.
Figure 2:
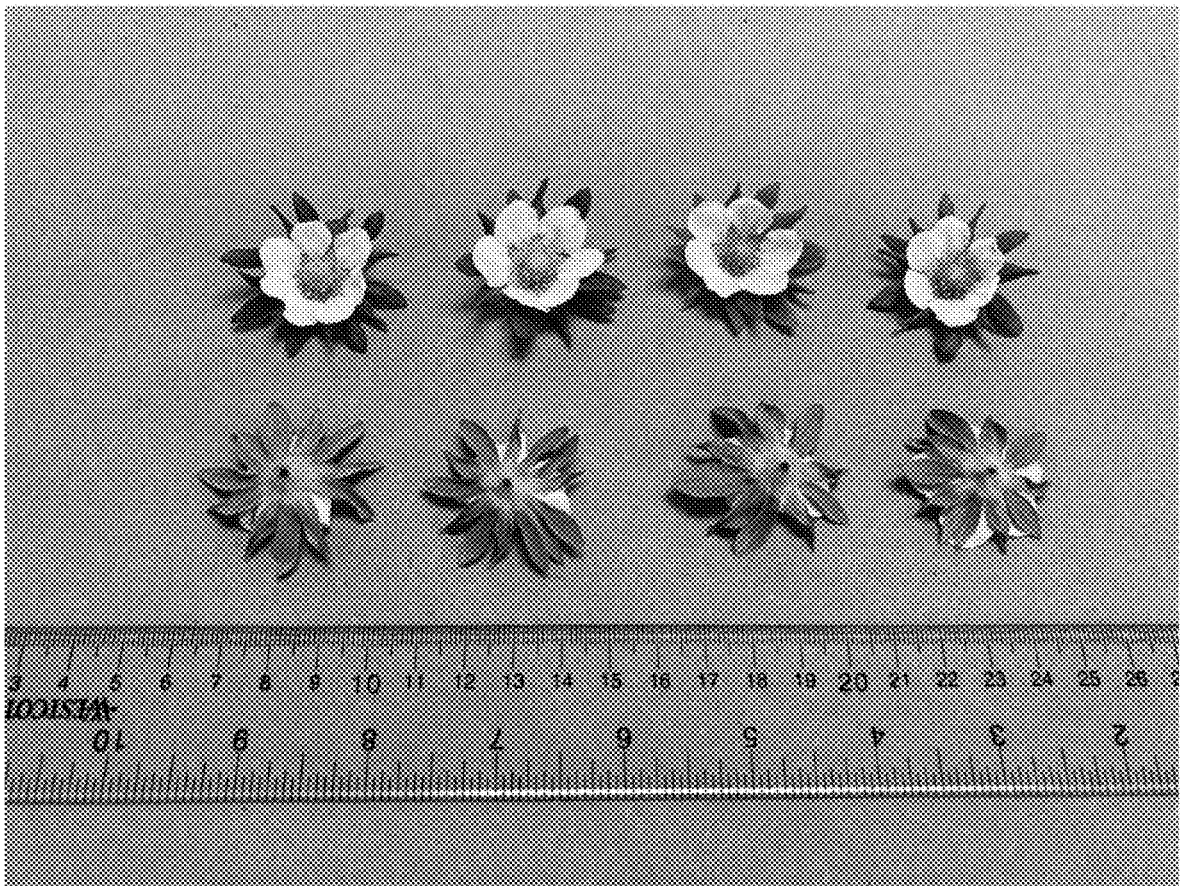
FIG. 2 shows upper and lower surfaces of flower and flower parts of 'S4A-334', taken in the month of March 2024.
Figure 3:
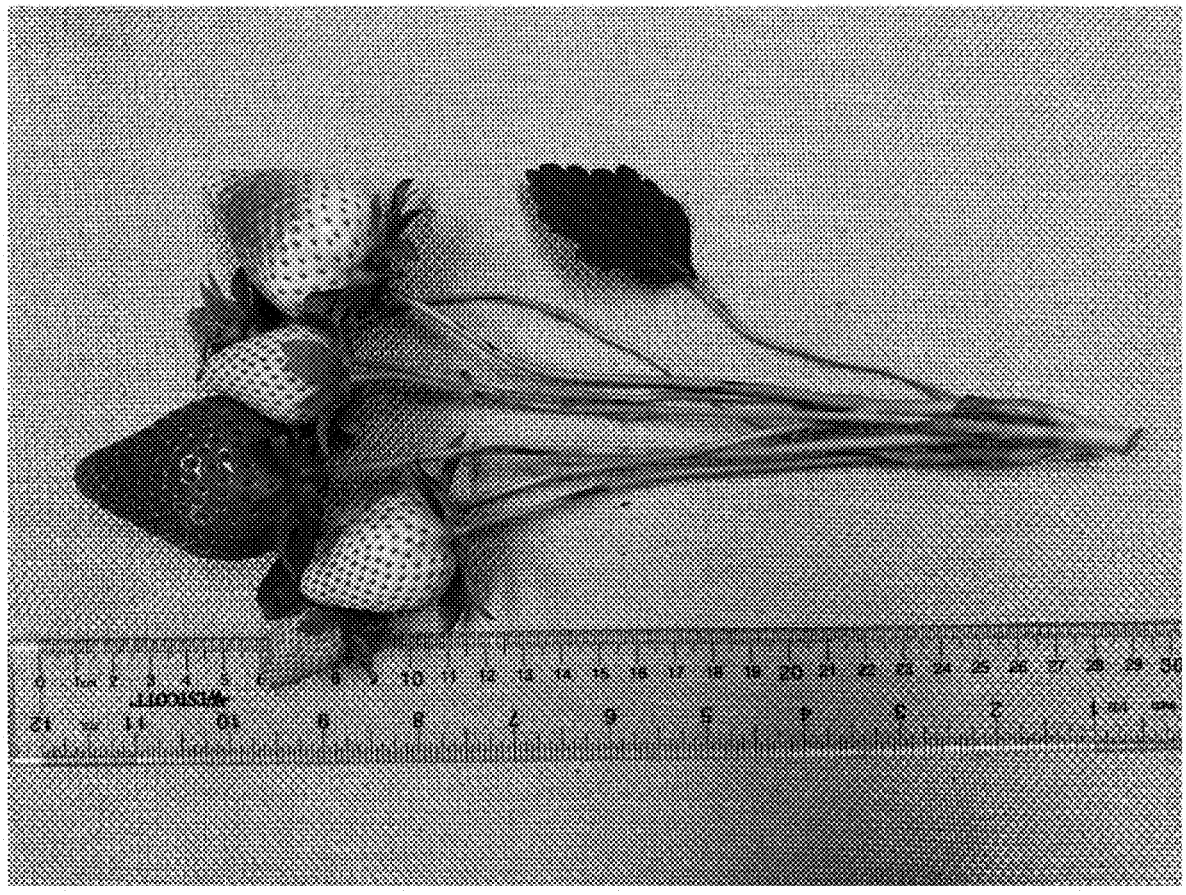
FIG. 3 shows typical fruiting truss and truss parts of 'S4A-334', taken in the month of April 2024.
Figure 4:
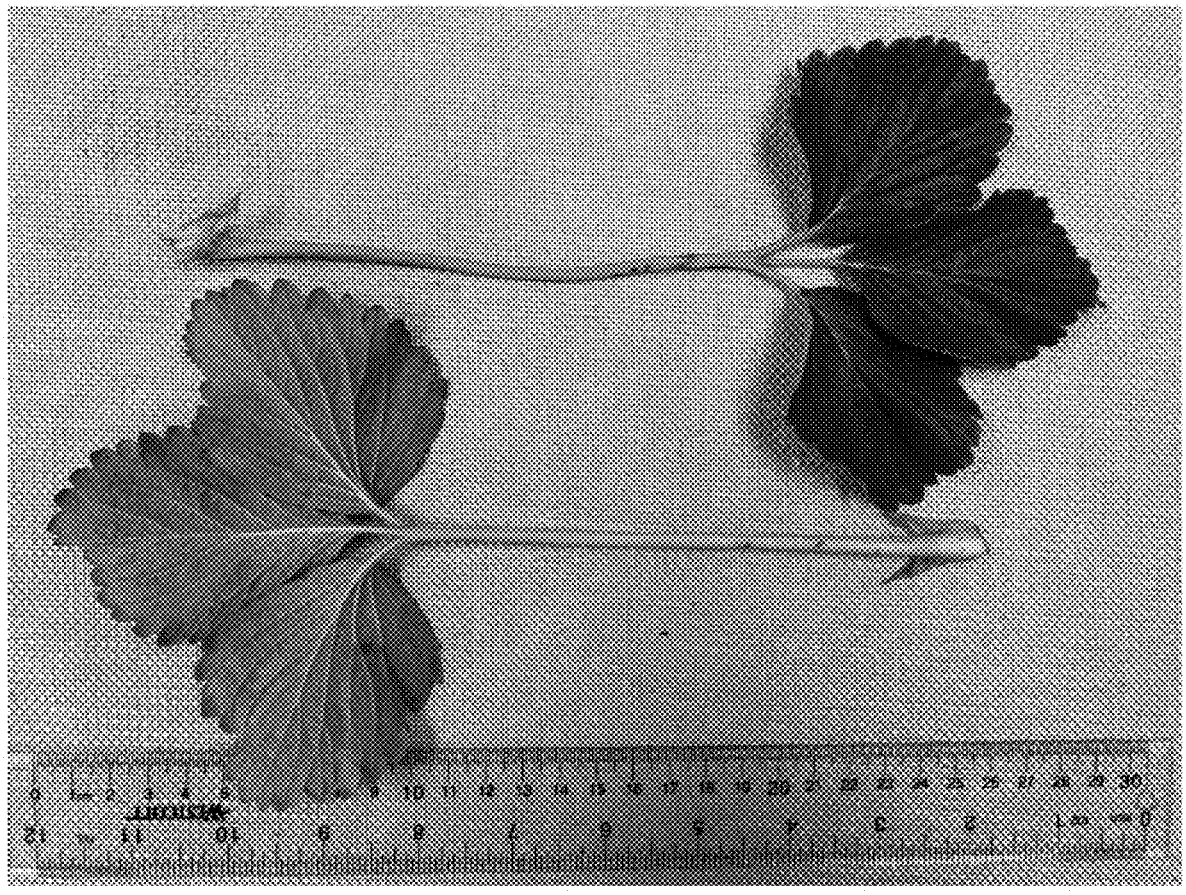
FIG. 4 shows upper and lower surfaces of leaf and leaf parts of 'S4A-334', taken in the month of April 2024.
Figure 5:
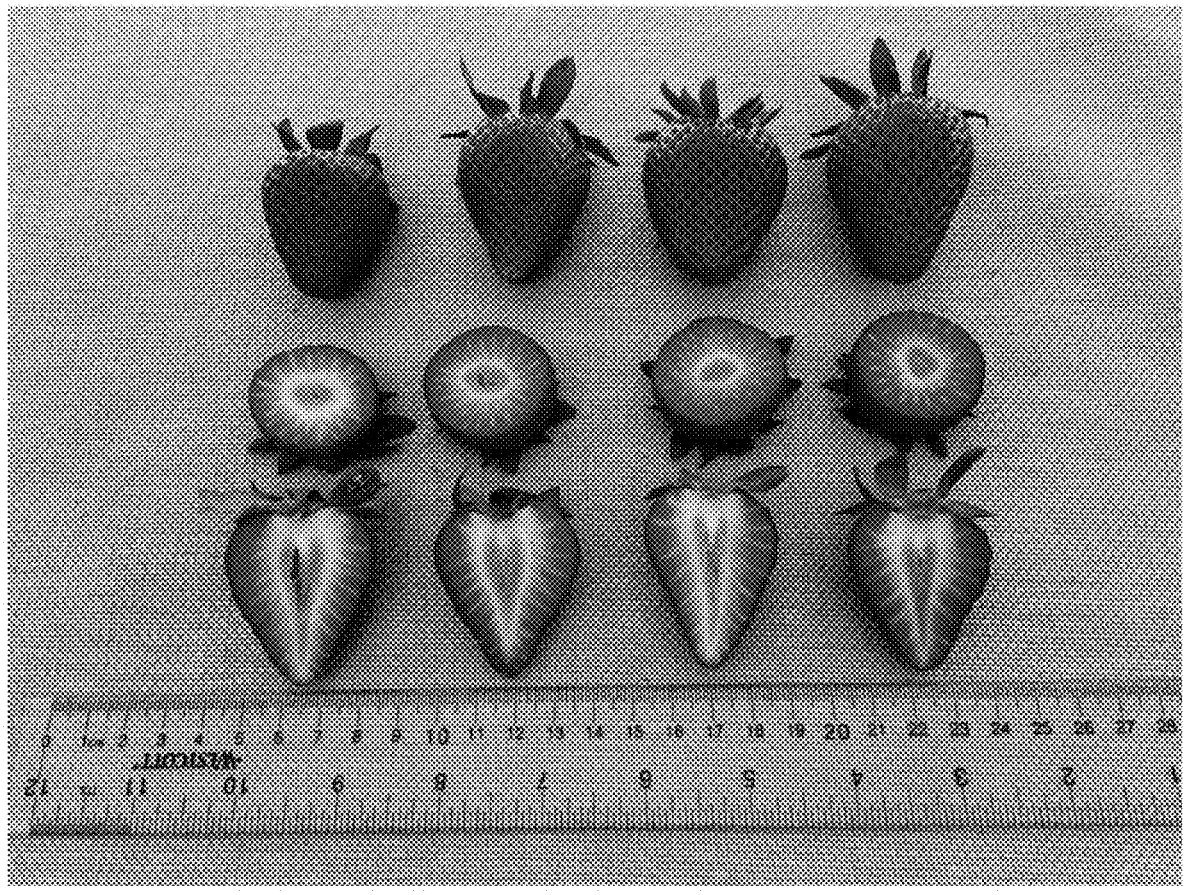
FIG. 5 shows internal and external mature fruit characteristics of 'S4A-334', taken in the month of May 2024.
Figure 6:
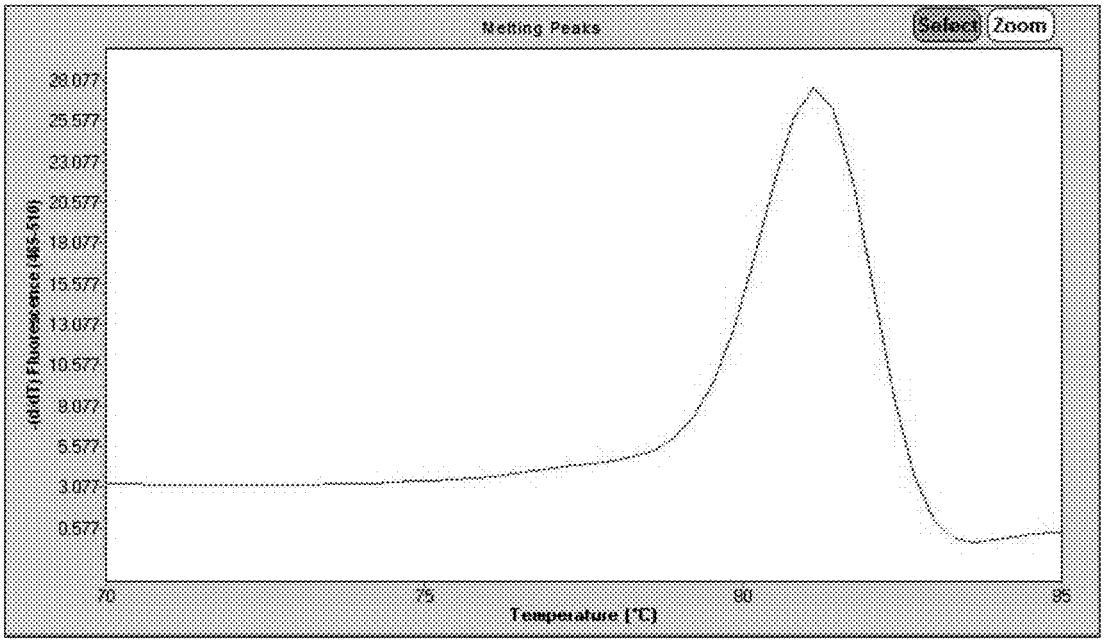
Figure 6:
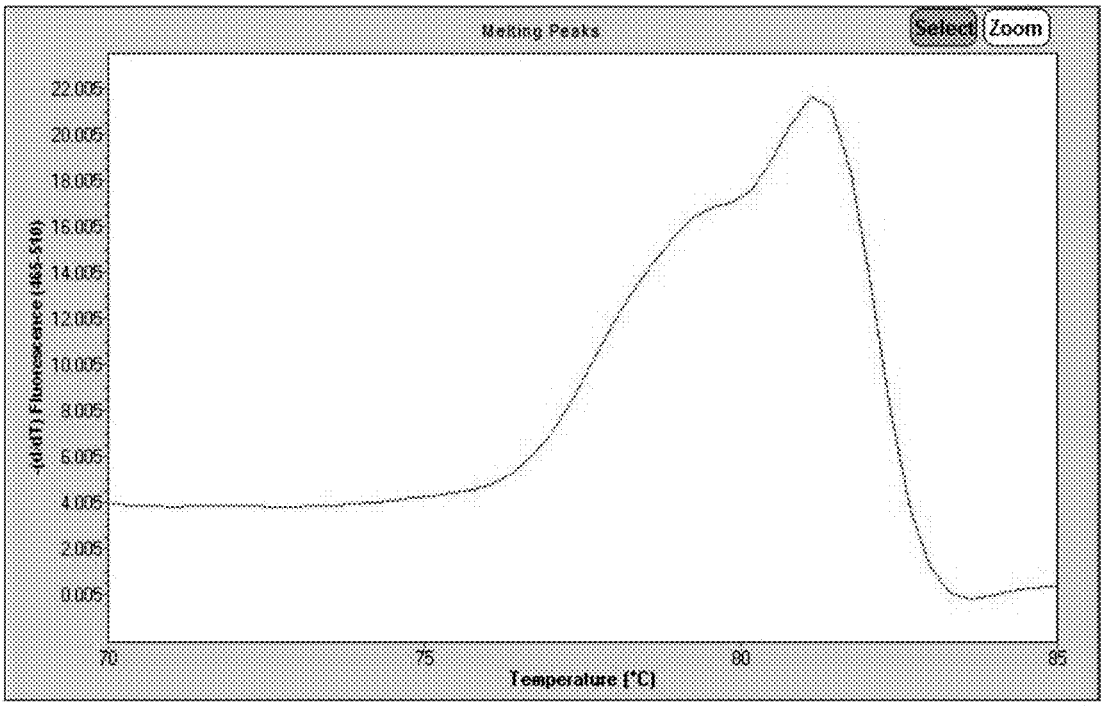
Figure 6:
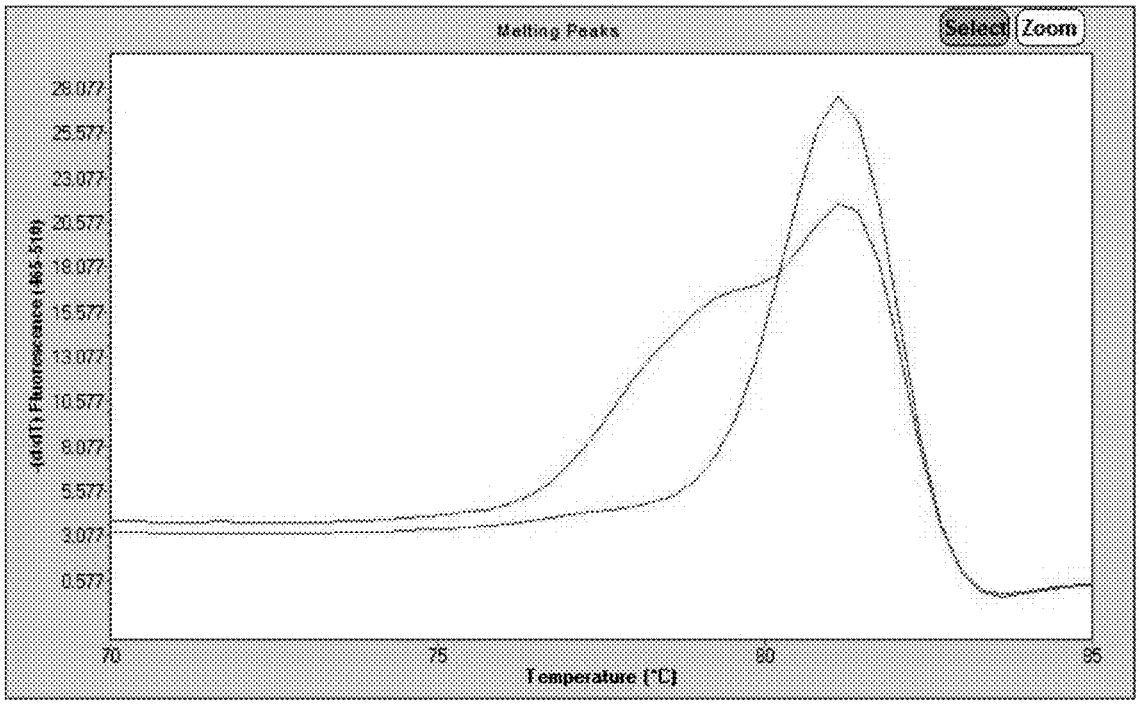

FIG. 6 demonstrates the genotypic differences between the two varieties described in Table 1. Primers for polymerase chain reaction (PCR) were created on either side of the genetic edit, to amplify the sequence that was edited.

FIG. 6A shows the PCR high-resolution melting (HRM) curve result for 'Inspire'.

FIG. 6B shows the PCR-HRM curve result for the edited 'S4A-334' line.

FIG. 6C shows the PCR-HRM results of these two varieties compared to each other. The results of this molecular DNA test clearly demonstrate that these two varieties are genotypically different from one another

DETAILED BOTANICAL DESCRIPTION

The new variety 'S4A-334' has not been observed under all possible environmental conditions. The characteristics of the new variety 'S4A-334' may vary in detail, depending upon variations in environmental factors, including weather (temperature, humidity and light intensity), day length, soil type and location. In addition, the characteristics of any comparison variety included in Table 1 and of the present invention may vary in detail, depending upon variations in environmental factors, including weather (temperature, humidity and light intensity), day length, soil type and location.

The aforementioned photographs, together with the following phenotypic and genotypic description of the new variety 'S4A-334', unless otherwise noted, are based on observations taken during the 2024 growing season in Ventura County, California. These measurements and ratings were taken from plants of 'S4A-334' dug from a high-elevation nursery located in Siskiyou County, California during early October 2023 and planted approximately four to five days later in Ventura County, California. The approximate age of the observed plants is five to six months. Yield observations including average weight and marketable yield, along with fruit quality characteristics including soluble solids, are averaged from three years of data collected from the 2022 through 2024 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London, Sixth Edition (2019 Reprint).

The following characteristics describe fruit, plant, stolon, foliage, fruiting truss, flower, reproductive organs and pest and disease characteristics of the new strawberry 'S4A-334'.

Fruit Characteristics:

*Color of mature fruit.*—RHS N34B (orange red).
*Color of internal flesh (excluding core).*—RHS 34C (light red).
*Color of core.*—RHS 39B (light red).
*Average length (cm).*—4.8.
*Average width (cm).*—3.6.
*Size.*—Medium.
*Average length/width ratio.*—1.33 (Much longer than broad).
*Hollow center average length (mm)*—17.2.
*Hollow center average width (mm)*—4.2.
*Hollow center expression.*—Weak.
*Season average weight (gm).*—29.3.
*Marketable yield season (gm/plant).*—1,121.
*Predominant shape.*—Conical.
*Difference in shape between primary and secondary fruit.*—None or very slight.

*Band without achenes.*—Narrow.
*Evenness of surface.*—Even or very slightly uneven.
*Evenness of color.*—Even or very slightly uneven.
*Glossiness.*—Strong.
*Insertion of achenes.*—Level with surface.
*Average calyx diameter* (*cm*).—5.3.
*Position of calyx attachment.*—Inserted.
*Attitude of sepals.*—Ranges from outward to upward.
*Size of calyx in relation to fruit diameter.*—Ranges from slightly larger to much larger.
*Adherence of calyx* (*when fully ripe*).—Strong.
*Firmness of flesh.*—Ranges from firm to very firm.
*Keeping quality.*—Excellent.
*Fruit market.*—Fresh.
*Post-harvest fruit longevity* (*at* 1 to 3 degrees Celsius) .—10 to 14 days.
*Distribution of red color of the flesh.*—Marginal and central.
*Sweetness.*—Very good.
*Soluble solids* (% *Brix*).—8.3.
*Achene color, shaded side.*—RHS 153A (yellow green group).
*Achene color, sun-exposed side.*—RHS 184A (greyed purple group).
*Achene average length* (*mm*).—1.6.
*Achene average width* (*mm*).—0.9.
*Achene average weight* (*mg*).—0.6.
*Achene average quantity per berry*—348.
*Achene shape.*—Elliptic.
*Time of beginning of flowering.*—Early (Late November in Ventura County, California).
*Time of beginning of fruit ripening.*—Early (December in Ventura County, California).
*Flowering season.*—November to May (in Ventura County, California).
*Harvest season.*—December to May (in Ventura County, California).
*Harvest maturity.*—Mid (March in Ventura County, California).
*Plant hardiness.*—Zone 10 (USDA Plant Hardiness Zone Map).
*Type of bearing.*—Partially remontant.

Plant Characteristics:
*Average height* (*cm*).—23.0.
*Average spread* (*cm*).—33.9.
*Size.*—Medium.
*Habit.*—Upright.
*Density.*—Medium.
*Vigor.*—Medium.

Stolon Characteristics:
*Color.*—RHS 146C (yellow green group).
*Anthocyanin coloration.*—RHS 181B (greyed red group).
*Anthocyanin intensity.*—Medium to weak.
*Pubescence.*—Medium.
*Attitude of hairs.*—Upward.
*Flowering runners.*—Present.
*Average quantity in nursery* (*per square foot*).—5 to 6 (medium)
*Average diameter at first bract* (*mm*).—2.9 (ranges from medium to thin).
*Length from mother plant to first daughter* (*cm*).—31.9.

Terminal Leaflets Characteristics:
*Average length* (*cm*).—7.2.
*Average width* (*cm*).—5.9.
*Average area terminal* ($cm^2$).—42.2.
*Average length/width ratio.*—1.21 (much longer than broad).
*Shape.*—Obovate.
*Shape of base.*—Acute.
*Shape of apex.*—Obtuse.
*Margins* (*shape of teeth*).—Obtuse (serrate to crenate).
*Average serrations per leaf.*—20.2.

Foliage Characteristics:
*Color of upper surface.*—RHS NN137B (medium green).
*Color of lower surface.*—RHS 147B (yellow green group).
*Color of venation, upper surface.*—RHS 137D (green group).
*Color of venation, lower surface.*—RHS 145C (yellow green group).
*Number of leaflets.*—3.
*Foliage size.*—Medium.
*Average length* (*cm*).—10.9.
*Average width* (*cm*).—15.0.
*Average area foliage* ($cm^2$).—164.7.
*Shape in cross section.*—Flat to slightly convex.
*Interveinal blistering.*—Medium.
*Pubescence of upper surface.*—Light.
*Pubescence of lower surface.*—Light.
*Venation pattern.*—Pinnate reticulate.
*Leaf glossiness.*—Medium.
*Leaf variegation.*—Absent.
*Leaf rugosity*—Medium.

Petiole Characteristics:
*Petiole color.*—RHS 144A (yellow green group).
*Average length* (*cm*).—15.4.
*Average diameter* (*mm*).—3.5.
*Average size.*—Medium.
*Attitude of hairs.*—Strongly outward.
*Frequency of bract leaflets.*—0% occurrence (none).
*Size of bract leaflets.*—N/A.
*Pubescence.*—Moderate.
*Petiolule color.*—RHS 144A (yellow green group).
*Petiolule average length* (*mm*).—14.1.
*Petiolule average diameter* (*mm*).—1.5.

Stipule Characteristics:
*Color*—RHS 146C (yellow green group).
*Anthocyanin coloration.*—RHS 56B (red group).
*Anthocyanin intensity.*—Absent or very weak.
*Average length* (*mm*).—16.8.
*Average width* (*mm*).—11.0.
*Shape.*—Triangular.
*Pubescence.*—Light.
*Shape of base.*—N/A.
*Shape of apex.*—Acute.
*Margins.*—Entire.

Fruiting Truss Characteristics:
*Anthocyanin coloration.*—RHS 181C (greyed red group).
*Anthocyanin intensity.*—Absent or very weak.
*Average length at maturity* (*cm*).—30.4.
*Position relative to foliage.*—Above.
*Flower quantity* (*season average per plant*).—63.9 (ranges from medium to many).
*Average fruit quantity per truss.*—6.3 (medium).
*Attitude at first pick.*—Prostrate.
*Primary pedicel color.*—RHS 146D (yellow green group).

*Primary pedicel average length* (*cm*).—19.5.
*Primary pedicel average diameter* (*mm*).—2.8.
*Pedicel attitude of hairs.*—Upward.
*Pedicel pubescence.*—Weak.
*Primary peduncle color.*—RHS 146D (yellow green group).
*Primary peduncle average length* (*cm*).—1.7.
*Primary peduncle average diameter* (*mm*).—8.2.
*Peduncle pubescence.*—Weak.

Flower Characteristics:
*Petal color, upper surface.*—RHS NN155C (white group).
*Petal color, lower surface.*—RHS NN155C (white group).
*Petal average length* (*mm*).—12.3.
*Petal average width* (*mm*).—11.1.
*Petal average length/width ratio.*—1.1 (as long as broad).
*Average petal quantity per flower.*—5.9.
*Petal shape.*—Obovate.
*Petal pubescence.*—Smooth.
*Petal shape of base.*—Obtuse.
*Petal shape of apex.*—Routund.
*Petal margins.*—Entire.
*Sepal color, upper surface.*—RHS 137B (green group).
*Sepal color, lower surface.*—RHS 138B (green group).
*Sepal average length* (*mm*).—17.5.
*Sepal average width* (*mm*).—6.5.
*Sepal average length/width ratio.*—2.70.
*Average sepal quantity per flower.*—11.3.
*Sepal shape.*—Ovate.
*Sepal pubescence.*—Light.
*Sepal shape of apex.*—Acute.
*Sepal margins.*—Entire.
*Flower bud color.*—RHS 145A (yellow green group).
*Flower bud shape.*—Cup.
*Flower bud average length* (*mm*).—21.9.
*Flower bud average diameter* (*mm*).—9.3.
*Corolla average diameter* (*mm*).—31.2 (large).
*Flower average depth* (*mm*).—11.3 (medium).
*Calyx average diameter* (*mm*).—43.1.
*Size of calyx relative to corolla.*—Larger.
*Arrangement of petals.*—Ranges from touching to overlapping.
*Size of inner calyx relative to outer calyx.*—Ranges from same to smaller.

Reproductive Organs:
*Anther color.*—RHS 14A (yellow orange group).
*Filament color.*—RHS 145C (yellow green group).
*Stamen.*—Present.
*Filament average length* (*mm*).—1.8.
*Anther average length* (*mm*).—1.0.
*Anther average width* (*mm*).—0.4.
*Anther shape.*—Elliptic.
*Pollen amount.*—Abundant.
*Pollen color.*—RHS 14A (yellow orange group).
*Ovary color.*—RHS 147C (yellow green group).
*Style color.*—RHS 151D (yellow green group).
*Pistil average quantity per flower.*—348.
*Pistil average length* (*mm*).—1.1.
*Style average length* (*mm*).—0.7.
*Stigma average diameter* (*mm*).—0.3.
*Stigma shape.*—Rounded.

Disease and Pest Reactions:
*Powdery mildew* (*Sphaerotheca macularis*).—Moderately resistant.
*Botrytis fruit rot* (*Botrytis cinerea*)—Moderately susceptible.
*Fusarium wilt* (*Fusarium oxysporum*).—Susceptible.
*Two-spotted spider mite* (*Tetranychus urticae*).—Moderately susceptible.

We claim:

1. A new and distinct strawberry plant named 'S4A-334', as described and illustrated herein.

* * * * *

A

B

C